United States Patent [19]

Padilla

[11] Patent Number: 4,641,639
[45] Date of Patent: Feb. 10, 1987

[54] AMBULATORY BRACE ASSEMBLY

[76] Inventor: Rigoberto Padilla, 801 West 48 St., Hialeah, Fla. 33012

[21] Appl. No.: 806,867

[22] Filed: Dec. 9, 1985

[51] Int. Cl.$^4$ ............................................. A61F 5/04
[52] U.S. Cl. ................................. 128/83.5; 128/87 R
[58] Field of Search ............... 128/87 R, 83, 82, 83.5, 128/89 R, 90, 80 R, 80 A, 157, 165

[56] References Cited

U.S. PATENT DOCUMENTS

| | | | |
|---|---|---|---|
| 2,189,053 | 2/1940 | Bryant | 128/83.5 |
| 2,423,354 | 7/1947 | Van Hoesen | 128/82 X |
| 3,351,055 | 11/1967 | Gottfried | 128/87 R |
| 3,643,656 | 2/1972 | Young et al. | 128/90 |
| 3,780,728 | 12/1973 | Stader | 128/83.5 |
| 3,955,565 | 5/1976 | Johnson, Jr. | 128/89 R |
| 4,217,893 | 8/1980 | Payton | 128/165 X |
| 4,576,153 | 3/1986 | Zagorski et al. | 128/87 R |

FOREIGN PATENT DOCUMENTS 2808968  9/1979  Fed. Rep. of Germany ........ 128/83

Primary Examiner—Robert A. Hafer
Assistant Examiner—Kathleen J. D'Arrigo
Attorney, Agent, or Firm—John Cyril Malloy

[57] ABSTRACT

An ambulatory brace of the type designed to fit in at least partially enclosing relation about the lower leg and foot of a patient so as to maintain this area substantially immobilized. The subject brace is specifically designed to eliminate all force or pressure being applied to the heel area of the foot so as to allow consolidation or healing of the calcaneum region by maintaining this region substantially free of weight or force being exerted thereon. A support assembly is incorporated into the brace so as to transfer or direct axial load on the brace directly to the tarso-metatarsal region of the foot.

18 Claims, 6 Drawing Figures

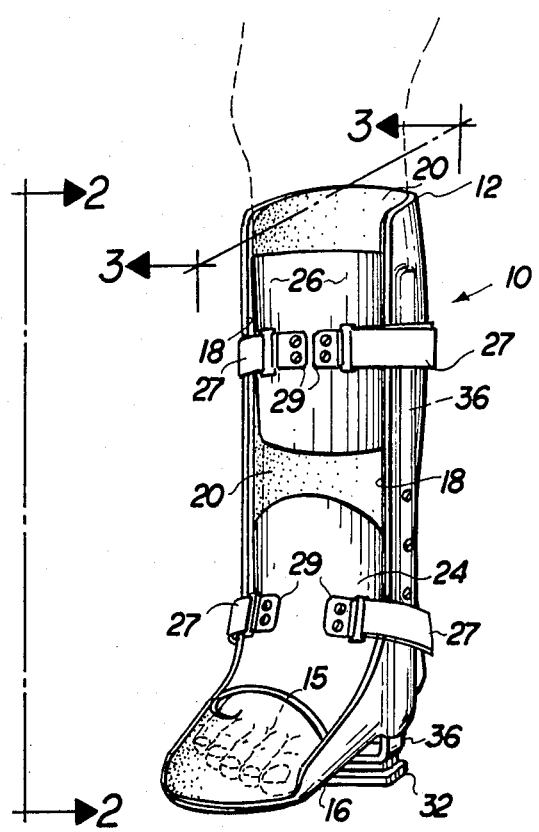
FIG. 1
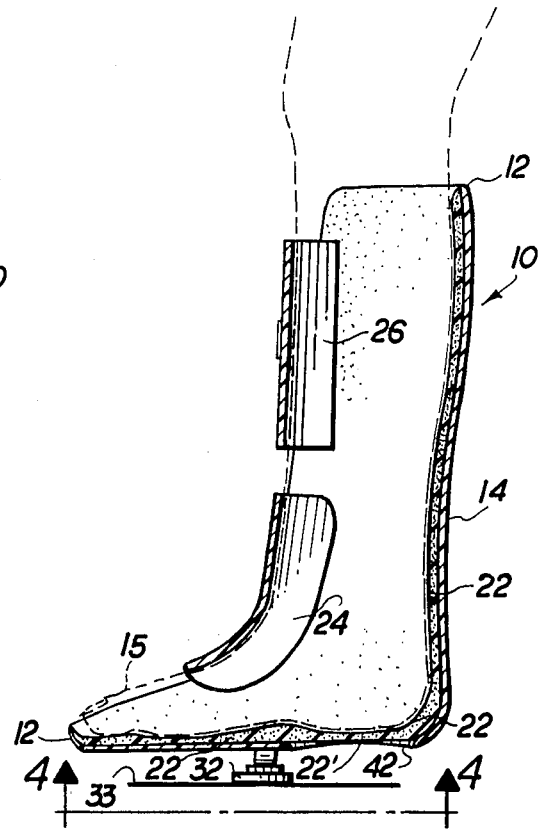
FIG. 3
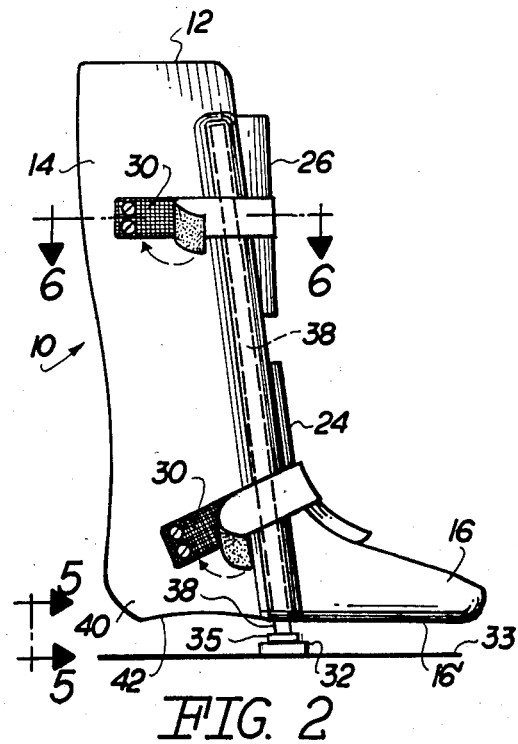
FIG. 2
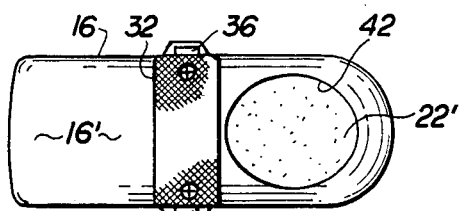
FIG. 4
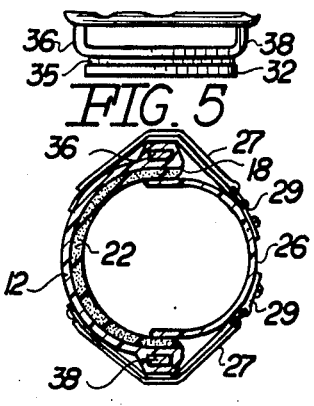
FIG. 5
FIG. 6

AMBULATORY BRACE ASSEMBLY

BACKGROUND OF THE INVENTION

1. Field of the Invention

The present invention is directed towards a brace assembly which is ambulatory and structured to immobilize the foot and maintain the heel portion of the foot free of any weight or forces being exerted thereon so as to allow healing or consolidation of fractures of the calcaneus.

2. Description of the Prior Art

The prior art is replete with casts and brace assemblies which are specifically designed to support areas of the human body for the purpose of allowing healing or consolidation of fractures in bones. Attendant to the procedure for which most prior art braces are designed is the immobilization of a specific area or portion of the body. In addition, certain brace assemblies are also designed to allow ambulatory movement of the patient and, even to some extent, utilization of the member or portion of the body involved in the fracture or like injury.

In the medical profession it is acknowledged that one particular area, namely, the heel portion or calcaneum region of the foot, is particularly difficult to heel without keeping the patient from walking or putting weight on the injured foot for a prolonged period of time. Naturally, such a situation is highly undesirable from the patient's standpoint since ambulatory movement is greatly preferred during the healing process. However, due to the location of the heel and the natural tendency of the weight of the patient to be a least partially absorbed by the heel portion of the foot, pressure is normally brought to bear on the calcaneus region during such normal activities as standing or walking.

Accoringly, there is a great need in the field of orthopedics and rehabilitation for a brace assembly capable of allowing ambulatory movement of the patient while at the same time maintaining the injured foot immobilized and the heel portion or calcaneum region of the foot free of any weight or load forces when the patient stands or walks. Such a preferred brace assembly should be of lightweight construction and structured to be easily affixed and removed from the injured foot without undue discomfort to the patient.

SUMMARY OF THE INVENTION

The present invention is directed towards a brace assembly which allows ambulatory movement of the patient and which immobilizes an injured foot in a manner which maintains the calcaneum region or heel portion of the foot free of any load forces being exerted thereon in order that fractures or injury of the calcaneus may consolidate or heal.

The brace assembly comprises a cast which is dimensioned and structured to define essentially a partial cast in that the entire front face of the cast, along its length, is open. This open front face thereby facilitates positioning of the injured foot and lower leg of the patient into and out of the cast without requiring total encapsulation of the foot or lower limb of the patient. The cast is formed into a substantially L-shaped configuraton and may somewhat resemble an open faced boot. A first portion of the cast extends from the heel and ankle portion upwardly to approximately the calf of the leg. A second portion of the cast extends from the heel portion outwardly to support and at least partially enclose the foot of the patient beyond the metatarsal region.

A restraining means, preferably in the form of a plurality of restraining elements extend across the open face into retaining engagement with the front portion of the foot received within the cast.

An important feature of the present invention is the provision of a support assembly which includes a support platform secured to and extending outwardly from an undersurface of the second portion or foot portion of the cast. The support platform is disposed substantially beneath the metatarsal region of the foot or between the calcaneum region (heel portion) and the phalanges (toes). Further, the support platform extends outwardly from the undersurface of the second portion of the cast a sufficient distance to maintain the heel portion of the cast out of contact with the ground or other supporting surface on which the patient stands or walks.

Further, the subject support assembly includes two leg elements fixedly attached to the platform and extending upwardly therefrom along oppositely disposed lateral portions of the cast. These support legs extend to a height at least equal to the ankle and preferably thereabove to the calf region. The disposition and angular orientation of the support legs and their cooperative interengagement with the support platform allows any axial load placed on the brace, due to the standing or walking of the patient, to effectively bypass the calcaneus region of the foot and be transferred primarily to the tarso-metatarsal region. This allows the calcaneum region to remain free of the vast majority of external stress received by the foot. Such stress or force would be painful and interfere with the consolidation of a cancaneus fracture and prevent the patient from being ambulatory.

BRIEF DESCRIPTION OF THE DRAWINGS

For a fuller understanding of the present invention reference is made to the following detailed drawings in which:

FIG. 1 is an isometric view of the brace assembly of the present invention surrounding a foot and calf portion represented in broken lines.

FIG. 2 is a side plan view of the embodiment of FIG. 1.

FIG. 3 is a sectional view along line 3—3 of FIG. 1.

FIG. 4 is a bottom view along line 4—4 of FIG. 3.

FIG. 5 is an end view along line 5—5 of FIG. 2, showing details of the portion of the support assembly of the present invention.

FIG. 6 is a sectional view along line 6—6 of FIG. 2.

Like reference numerals refer to like parts throughout the several views of the drawings.

DETAILED DESCRIPTION OF THE PREFERRED EMBODIMENT

As shown in FIGS. 1 through 6, the brace assembly of the present invention is generally indicated as 10 and is specifically designed, as set forth in detail hereinafter, to effectively immobilize the heel portion of the foot while allowing ambulatory movement of the patient on which the brace is mounted. All stress is effectively removed from the heel due to the weight of the patient while standing or walking.

The brace assembly comprises a cast 12 including a first portion 14 extending substantially from the heel upwardly in surrounding relation to the lower part of the leg to a height equal to approximately the calf. Such is clearly shown in phantom lines in FIGS. 1 and 3. In addition, the cast 12 includes a second portion 16 extending from the heel outwardly at substantially right angles to the first portion 14 and in surrounding and supporting relation to the foot of the patient as at 15.

As shown best in FIGS. 1 and 3, the cast 12 essentially comprises a partial cast in that it is structured and configured for partially surrounding relation to the lower portion of the leg and foot from the calf up to and beyond the toes of the foot. To accomplish fitting and removal of cast 12 from the leg, the cast includes an open face 18 extending along the entire length thereof. As set forth above, the transverse dimension of the open face is such that the foot and lower leg may readily pass through the open face 18 for fitting and removal of the cast 12 therefrom.

In order to add to the comfort as well as to provide proper support to the enclosed or encased portion of the leg and foot, the interior surface of cast 12 substantially conforms to the portion of the foot and leg which it surrounds. In order to accomplish an efficient conformance for adaptation of the inner surface 20 to the outer surface of the leg and foot, such inner surface is defined by a liner material which is flexible and relatively soft compared to the rigid material from which the cast 12 is formed. As shown, the liner 22 may extend along the entire length of cast 12 and define the exposed inner surface 20 as clearly shown in FIGS. 1 and 3. Alternately, such liner 22 may primarily be located underneath the surface of the foot and heel and surrounding engaging relation to the lower ankle and still come within the scope of the present invention.

The brace assembly of the present invention further includes retaining means in the form of at least one but preferably two retaining shields or elements 24 and 26 disposed in covering relation to the front portion of the foot, ankle, and/or shin as shown best in FIGS. 1 and 3. The retaining elements 24 and 26 are made from a substantially rigid material similar to or the same as the material from which cast 12 is formed. Further, retaining straps 27 serve to interconnect the retaining elements 24 and 26 in partially covering relation to the open face 18 and in overlying and retaining relation to the front portion of the patient's foot and leg. Conventional connector elements such as buckles and/or Velcro fasteners 29 and 30 respectively may be utilized to secure the straps in interconnecting relation between the cast 12 proper and the individual retaining elements 24 and 26.

An important feature of the present invention is a support assembly secured to the cast 12. The support assembly is specifically structured to allow weight to be placed on the brace assembly 10, due to its surrounding and supporting engagement with the injured limb of the patient. Such weight is placed on the brace assembly 10 and absorbed thereby such as when the patient stands or walks. Accordingly, the brace assembly 10 specifically allows ambulatory movement of the patient without putting any weight on the injured heel portion thereof as to be explained in greater detail hereinafter.

The support assembly includes a support platform 32 extending outwardly from the undersurface 16' of the second portion 16 of the cast 12 into engaging and supporting relation with a supporting surface 33. The support platform 32 may be made from rubber, leather, or any durable material which will stand up under continued abrasive and/or frictional engagement with the supporting surface 33. The support assembly includes a support brace 35 serving to interconnect the support platform 32 with the remainder of the support assembly to be described in greater detail hereinafter. It is important to note that the support platform 32 is located in outwardly extending relation to the undersurface 16' of the second portion 16 of the cast 12 directly in the area of the mid foot or metatarsal region of the foot. Accordingly, any weight placed on the injured foot will result in forces being exerted on the mid portion or metatarsal region of the foot. As a result, substantially all of the stress, force or pressure will be directed away from the injured heel portion. The above noted location of the support platform 32 relative to the under portion of the metatarsal region of the foot is clearly shown in FIGS. 1 through 4.

The support assembly further includes support legs which may be integrally or otherwise fixedly secured to the support brace 35. Such support legs 36 and 38 extend upwardly from the support platform along the sides of the cast 12 and in straddling relation to the outer surfaces or sides of the first and second portions of the cast 14 and 16. In order to fixedly secure and effectively have the support legs 36, 38 become a part of the cast, and thereby facilitate weight or force transfer, such legs are effectively encapsulated in the cast 12 even though they project somewhat outwardly from the corresponding sides thereof.

As shown in FIG. 6, the legs 36 and 38 are spaced apart from one another in a substantially parallel relation and are positioned adjacent to the open face 18 of the cast as they extend along substantially the entire length thereof towards the calf area or upper end of the first portion 14 of cast 12. Further, as shown in FIG. 2, the legs 36 and 38 are arranged at a substantially angular orientation rather than being perpendicular to the supporting surface when the cast 12 and support platform 35 are in an upright supporting or standing position. This angular orientation facilitates equal weight transfer to the metatarsal region of the foot and, as set forth above, accomplishes the desired goal of removing any weight or pressure from the heel area which is injured. As further shown in FIGS. 2 and 3, the angular orientation, and placement of the support legs 36 and 38 as well as the distance of outward extension of the platform 32 from the undersurface 16' of the second portion 16 of cast 12 enables the patient to take an almost normal stride while still preventing the heel area 40 from coming in contact with the supporting surface 33 during such stride. Therefore it is intended that only the support platform 32 come in force bearing engagement with the support surface 33. Further, as clearly shown in FIGS. 1, 2 and 3, the placement of the legs 36 and 38 are such as to be disposed substantially in front of a central axis of the lower leg within the first portion 14 and closer to the front open face 20 than the central axis of the lower leg portion as the legs 36 and 38 extend along their length to the point where the support platform 35 exits from the undersurface of the cast 12 directly beneath the metatarsal region of the foot 15 disposed within the second portion 16 of the cast 12. It should readily be apparent therefor and as pointed out hereinabove, force placed on the cast 12 due to standing or walking of the patient is thereby effectively directed away from the heel portion of the foot being retained and concentrated more towards and on the metatarsal region of the foot 15.

Another structural feature of the cast 12 provided to eliminate force being applied to the injured heel area of the foot is an apertured construction 42 (see FIG. 4) provided in the undersurface portion 16' immediately beneath the heel area. Such apertured construction 42 insures that any downward movement or weight transfer to the heel area will not cause its abutting engagement with a hard surface material from which the cast is formed. The only surface or structural portion of the brace assembly 10 coming in contact with the heel will be the liner material as at 22' as shown in FIGS. 3 and 4.

It is therefore to be understood that the following claims are intended to cover all of the generic and specific features of the invention herein described and all statements of the scope of the invention as a matter of language, might be said to fall therebetween.

Now that the invention has been described,
What is claimed is:

1. An ambulatory brace assembly of the type primarily designed to immobilize the foot of a patient and direct forces to which the brace assembly is subjected away form the heel during walking and like activities of the patient, said assembly comprising:
   (a) a cast structure having an open front face and an at least partially hollow interior configured to receive and at least partially enclose a lower leg and foot of the patient,
   (b) said cast comprising a substantially L-shaped configuration including a first portion thereof having a longitudinal dimension sufficient to extend from a calf portion of the leg to a location beneath a heel portion of the foot,
   (c) said L-shaped configuration comprising a second portion extending outwardly from said first portion along at least a majority of the length of the received foot,
   (d) said hollow interior further including an interior surface extending along the length of said first and said second portions and configured in substantial conformance to a correspondingly positioned exterior surface of the lower leg and foot received within said cast,
   (e) a support assembly comprising a support platform disposed outwardly from an undersurface of said second portion, and two support legs each including correspondingly positioned distal ends fixedly secured to said support platform, said support legs extending outwardly from said support platform in spaced, substantially parallel relation to one another and each being fixedly secured to an opposite side of said cast, said support legs disposed and structured in cooperative relation to said support platform to bear the majority of the axial load of said cast when supporting the patient during walking or standing,
   (f) said support platform mounted a first predetermined distance from one end and adjacent heel of said second portion and extending outwardly from said undersurface a second predetermined distance and into engagement with a supporting surface on which the patient is walking,
   (g) said first predetermined distance being of sufficient dimension from the heel and one end of said second portion to position said support platform beneath the metatarsal region of the foot and direct forces away from the heel portion of the foot,
   (h) said second predetermined distance being of sufficient dimension to maintain said one end of said second portion out of contact with the supporting surface during travel of said cast when the patient is walking,
   (i) said undersurface of said second portion including an apertured construction disposed directly beneath the heel of the foot received within said cast and being of sufficient dimension to prevent forced engagement between the heel of the foot and any cast portion located in the vicinity immediately below the heel of the foot, and
   (j) retaining means secured to said cast and extending across said open front face for maintaining the lower leg and foot of the patient within said hollow interior.

2. An assembly as in claim 1 wherein said open front face extends along at least a major portion of the length of said cast and between oppositely disposed distal ends of said first and second portions.

3. An assembly as in claim 2 wherein said open front face includes a transverse dimension along the length thereof being sufficient to allow passage therethrough and entry of the lower leg and foot of the patient into said hollow interior of said cast.

4. An assembly as in claim 2 wherein said retaining means comprises a plurality of retaining elements movably mounted on said cast and each structured and disposed to extend substantially transversely across said open front face at spaced locations from one another.

5. An assembly as in claim 4 wherein each of said retaining elements comprises a flexible material strap secured to one side of said cast adjacent said open front face, securing means mounted on said casing on an opposite side thereof opposite to said one side and adjacent said open front face, each of said straps removably connectable to said securing means and thereby disposable across said front open face.

6. An assembly as in claim 1 further comprising a liner formed of relatively soft, resilient material secured to exposed surface portions of said hollow interior and defining said interior surface of said first and second portions.

7. An assembly as in claim 1 wherein said support platform and said support legs are fixedly secured to said cast in a substantially straddling disposition relative to said second portion, said support platform disposed to direct axial loads on said cast due to the supporting of the patient, to the metatarsal portion of the foot and away from the heel thereof.

8. An assembly as in claim 7 wherein said support legs each include an elongated configuration and each support leg is secured to and extends along oppositely disposed lateral portions of said cast for a distance at least equal to the height of the ankle received within said cast.

9. An assembly as in claim 8 wherein the longitudinal dimension of said legs are sufficient to extend along a major portion of the length of said first portion of said cast.

10. An assembly as in claim 8 wherein said support legs are disposed in substantially coplanar relation to one another and extend outwardly from said support base along the length of said first portion at an angular orientation from vertical.

11. An assembly as in claim 10 wherein said angular orientation of said support legs relative to vertical is substantially 5 degrees.

12. An assembly as in claim 1 wherein said retaining means comprises a shield assembly including at least one shield element interconnected to said cast across said open front face and in substantially covering relation to a front portion of a limb received within said cast.

13. An assembly as in claim 12 wherein said one shield element includes an interior surface having a substantially concave cross-sectional configuration along its length, said interior surface disposable in engaging relation with a front portion of the limb of the patient.

14. An assembly as in claim 13 wherein said shield assembly comprises a second shield element formed of substantially rigid material and movably attached to said cast for selective positioning across said open front face, said second shield element disposed in spaced relation to said one shield element and in covering relation to a front portion of an ankle of the patient.

15. An assembly as in claim 14 wherein said second shield element comprises an interior surface disposed in engaging relation to the ankle and including a substantially concave transverse and longitudinal cross-sectional configuration.

16. An assembly as in cliam 8 wherein at least one of said shield assemblies is formed from a substantially rigid material.

17. An assembly as in claim 1 wherein said support legs extend along said first portion and extend outwardly from said second portion at an angular orientation from vertical when said cast is disposed in a normally upright position.

18. An assembly as in claim 17 wherein said angular orientation of said support legs relative to vertical is substantially 5 degrees.

* * * * *